United States Patent [19]

Fussi et al.

[11] 4,264,733
[45] Apr. 28, 1981

[54] NATURAL HEXURONYL HEXOSAMINOGLYCANE SULFATE, METHOD FOR THE PREPARATION THEREOF AND RELATED THERAPEUTICAL USES

[75] Inventors: Fernando Fussi, Lesmo; Gianfranco Fedeli, Milan, both of Italy

[73] Assignee: Hepar Chimie S.A., Faibourg, Switzerland

[21] Appl. No.: 134,336

[22] Filed: Mar. 26, 1980

Related U.S. Application Data

[62] Division of Ser. No. 930,540, Aug. 2, 1978.

[30] Foreign Application Priority Data

Aug. 10, 1977 [GB] United Kingdom ............... 33615/77

[51] Int. Cl.$^3$ ............................................ C12P 19/04
[52] U.S. Cl. .................................................... 435/101
[58] Field of Search ......................................... 435/101

[56] References Cited

U.S. PATENT DOCUMENTS

| | | | |
|---|---|---|---|
| 3,066,076 | 11/1962 | Monnier | 536/21 |
| 3,174,903 | 3/1965 | Fischer et al. | 536/21 |
| 3,179,566 | 4/1965 | Horner et al. | 536/21 |
| 3,451,996 | 6/1969 | Sumyk et al. | 536/21 |
| 4,140,578 | 2/1979 | Yoshikumi et al. | 536/1 |

*Primary Examiner*—Lionel M. Shapiro
*Attorney, Agent, or Firm*—Cushman, Darby & Cushman

[57] ABSTRACT

Natural heteropolysaccharide, specifically hexuronyl hexosaminoglycane sulfate and, a process to obtain it, which substantially provides for the following steps:
(a) hydrolysis of an animal organ with a proteolytic enzyme, in water;
(b) precipitation of the hydrolyzed product with a water miscible solvent;
(c) solubilization of the precipitate in a solution of a salt of a strong mineral acid;
(d) addition of a quaternary ammonium halide to form a soluble complex and a precipitate which is separated;
(e) precipitation of such complex by dilution with water;
(f) isolation and solubilization of the precipitated complex in a salt solution according to step (c);
(g) precipitation of the final product with a water miscible solvent and drying thereof;

Such compound is utilized as active principle in pharmaceutical compositions, particularly suitable for the prevention of thrombotic states.

10 Claims, No Drawings

NATURAL HEXURONYL HEXOSAMINOGLYCANE SULFATE, METHOD FOR THE PREPARATION THEREOF AND RELATED THERAPEUTICAL USES

This is a division of application Ser. No. 930,540 filed Aug. 2, 1978.

The present invention relates to a natural heteropolysaccharide, more particularly to a natural hexuronyl hexosaminoglycane sulfate, as obtained by extraction of animal organs, which shows anticoagulant, antithrombotic and clearing activity.

Thrombosis often causes permanent invalidity and is one of the most frequent factors of death in the field of the cardiovascular diseases.

The generic term of thrombosis includes states of hypercoagulability, the origin of which is attributable to:

'Risk factors' which give place to a 'thrombogenic state', such as, for example, smoke, stresses, the prolonged use of contraceptives of progestin type, etc.

Hereditary factors, such as the absence or the lack of inhibitors (particularly antithrombin III).

Etiologic factors having various and sometimes not yet well clarified origin, such as modifications in platelet aggregation.

Factors related to a temporary slowing down of the blood circulation, such as takes place, for example, after surgical operations under narcosis.

The pathological consequences resulting from a 'thrombogenic' state as determined by one or more of the above listed factors can be the following:

pulmonary, cerebral, coronaric thromboembolism and infarction.

thrombophlebitis, varicose syndromes.

intravascular disseminated coagulation.

In view of such relevant phenomena, to date recourse may be made to two types of strategy:

1. The use of thrombolytic agents.
2. The prevention of thrombogenic states and of their consequences.

Due to the gravity and high rate of possible progress of the thrombosis, it is evident that the second type of strategy would be far the best.

In order to deal with, on prevention basis, the problem of the thrombosis, two classes of drugs are available at present: the oral anticoagulants (coumarin and derivatives thereof) and heparin. The oral anticoagulants (coumarin and derivatives) act at the hepatic level by blocking two factors of the coagulation: proconvertin and prothrombin. These anticoagulants, however, are unsuitable for a prolonged therapy, and furthermore, show a poor antithrombotic activity since their action does not concern other factors of the hemocoagulation particularly involved in the genesis of the thrombosis, mainly the XA and the platelet factors.

Under this point of view the heparin appears to be more advantageous since it acts on several plasmatic factors of the hemocoagulation, and particularly on the thrombin, on the XA factor and also on the XII, XI and IX factors, besides its action on the so called PF4 platelet factor. All these actions can be attributed to the specific capacity of the heparin of activating the inhibitor of the above listed coagulation factors. This inhibitor, which is present in the plasma, is called antithrombin III and requires the presence of heparin as co-factor for developing its action.

Unfortunately the heparin therapy is objectionable for two reasons: first of all, it is active only by parental route and the effect thereof has a duration not greater than 8 to 12 hours, whereby a time extended prophylaxis, involving two daily injections of heparin, is difficult to achieve. Furthermore, the heparin has not only an antithrombotic effect, but also a total anticoagulant action. Now, although this second action is sometimes favourable, in some cases the risk of hemorrhage, if the therapy is not suited to the particular patient, can be a serious problem in front of the indisputable advantages of prophylaxis of the thrombosis.

It has been found and it is the main subject of the present invention, that a heteropolysaccharide, more particularly a hexuronyl hexosaminoglycane sulfate, as obtained by extraction from animal organs, is not only endowed with anticoagulant, antithrombotic and clearing activity, but can be administered both orally and parenterally, it can be absorbed through the intestinal barrier and by topical way, and shows a ratio between antithrombotic activity and anticoagulant activity which is favourable in comparison with heparin.

For the identification of the product of the present invention reference is made to the following data:

Hexosamine after hydrolysis (reaction with p-dimethylaminobenzaldehyde): 27±3%

Organic $SO_4^{--}$ after hydrolysis (titration with naphtarsone): 27±4%

Acetyl groups after hydrolysis: 7±1%

Sodium (atomic absorption): 10±2%

Molar ratio huronic acids: hexosamine:sulfate:acetyl:sodium = about 1:1.2:2:1.2:3

Molecular weight range (chromatography by exclusion on gel): 8.000–16.000

Specific rotation $[\alpha]_D^{20} = -15/-30°$

Electrophoresis on cellulose acetate (buffer:pyridine acetic acid water=1:10:229, pH 4.5 and development with toluidine blue):

One main band with electrophoretic mobility $U = 1.90 - 1.95 \times 10^{-4}$ cm$^2$v$^{-1}$s$^{-1}$.

I.R. spectrum: characteristic bands are observed at 1740, 1647, 1555, 1375, 1235 and 1050 cm$^{-1}$.

Solubility: the heteropolysaccharide of the present invention is soluble in water, in diluted mineral acids and diluted fixed alkalis but insoluble in ethanol.

As regards the identification, the following test is furthermore useful: 1 ml of a 2% water solution of the product of the present invention is supplemented with 3 mls of 2% water solution of cetylpyridinium chloride heated to 40° C.: A bulky white precipitate is formed. The precipitate is separated by centrifugation and suspended in 3 mls of a 0.7 M KCl solution: the complete dissolution of the precipitate is obtained.

Another feature of the present invention relates to the extraction process for obtaining the above identified product. This process is characterized by the following steps:

(a) Hydrolysis of an animal organ, ground and suspended in water, with a proteolytic enzyme.

(b) Precipitation of the limpid liquid by a water miscible solvent.

(c) Solubilization of the precipitate in a solution of a salt of a strong mineral acid and of a mono- or divalent cation (e.g. sodium, ammonium, calcium) said saline solution having a ion concentration corresponding to that of 0.8 M NaCl.

(d) Addition at a temperature not higher than 80° C. of an excess of quaternary ammonium halide, selected from those having in their molecule at least one aliphatic group with more than 12 atoms, whereby a complex is formed which remains in solution, whereas the simultaneously formed precipitate is separated.

(e) Precipitation of the complex by dilution with water until a ion concentration not higher than that of 0.4 M NaCl is obtained.

(f) Isolation of the precipitated complex and solubilization thereof in a salt solution having the same characteristics of that of the step (c).

Precipitation of the desired product by a water miscible solvent and desiccation.

By particularly considering now the several steps of the above defined process, the following features are to be pointed out. The animal organ which is subjected to the hydrolysis is preferably fresh or deep-frozen. Amongst the useful animal organs, lungs and duodenum are preferred. The proteolytic enzyme is preferably selected from vegetal (papain, ficin, bromelin) or bacterial endopeptidases, and the conditions in which the hydrolysis is carried out depends on the type of enzyme. It is particularly preferred to perate the hydrolysis under mild heat, for periods not less than 3 hours, and until the value of the α-amino nitrogen (as determined by means of the Soerensen Method) no longer varies.

For the precipitation of the limpid liquid after hydrolysis the solvent to be used is selected between acetone, dioxane, methanol, ethanol and the like.

The quaternary ammonium halide of the step (d) is preferably selected from chlorides and bromides of cetylpyridinium and cetyltrimethylammonium. The related excess is of at least 0.5 g of quaternary amonium salt per Kg of starting animal organ. Lastly for the precipitation of the final product (step g) the use of acetone is preferred and the precipitate is vacuum-dried or lyophilized.

There are now given two examples, having illustrative but not limitative purpose, of the extraction process according to the present invention.

EXAMPLE 1

100 Kg of pork duodenum are ground and suspended into 50 liters of water. After heating to 40° C., 200 g of papain suspended into 25 liters of water are added. After heating the whole mixture to 60° C., the lysis is continued for 3 hours.

At the end, the mixture is heated to 90° C. for 15 minutes. The whole mass is filtered in a filterpress with 4 Kg of filter aid.

The limpid filtrate is concentrated to 50 liters, supplemented with 150 liters of ethanol and maintained on standing overnight.

After removal of the hydro-alcoholic upper liquid phase, the precipitate is carefully dried and suspended into 25 liters of water containing 1200 g of NaCl and filtered. The filtrate is supplemented under stirring with 25 liters of 0.8 M NaCl containing 50 g of cetyltrimethylammonium chloride and the mixture is heated to 40° C. The mixture is filtered in a filter-press with 2 Kg of filter aid and the limpid filtrate is added with 2 Kg of filter aid and diluted under stirring with 50 liters of water. After heating to 40° C., the precipitate is collected by vacuum filtration.

The cake of precipitate is suspended into 10 liters of 0.8 M NaCl and heated to 40° C. After filtration, to the limpid liquid, under stirring, 1.5 volumes of acetone are added, the mixture being maintained on standing overnight. The hydroacetonic liquid upper phase is removed and the precipitate is washed with 2×5 liters of 70% acetone and then dehydrated with anhydrous acetone. Then the pulverization and the vacuum desiccation are carried out.

Yield: 8 g of white-ivory, sligthly hydroscopic powder, having the following characteristics:
Solubility in water: Complete
$[\alpha]_D^{20} = -18°$
Huronic acids: 28%
Hexosamines: 30%
Organic $SO_4^{--}$: 26.5%
Anticoagulating activity: 25 U/mg (USP)
Antithrombotic/anticoagulant activity ratio (Yin's test/KCCT test)=2.
Clearing activity: 125 ILU/mg (international lipasemic units).

As regarding the clearing activity, it is related to the lipasemic activity, namely to the minimum value of international lipasemic units (ILU) which are found in 1 liter of plasma, by administering intravenously the substance to be tested to rats at the dose of 1 mg/Kg of body weight. In turn by international lipasemic unit, the lipasemic activity is that which causes 1 micromole of oleic acid to be hydrolyzed each minute.

EXAMPLE 2

50 Kg of bovine lung are ground and suspended into 75 liters of water. After heating to 40° C. 200 g of papain suspended into 25 liters of water are added and the mixture is heated to 65° C. for 3 hours. After this time the mixture is heated to 90° C. for 30 minutes.

The liquid is then filtered and the filtrate is concentrated to 50 liters and filtered again. The filtrate is supplemented with 100 liters of acetone and then maintained on standing overnight. After removal of the liquid upper phase, the precipitate is taken with 50 liters of 0.8 M NaCl containing 50 g of cetylpyridinium chloride. The mixture is then heated to 40° C. and filtered with 2 Kg of Standard Supercell (filter-aid).

The filtrate is diluted with 50 liters of water containing 500 g of Standard Supercell as a suspension. The precipitate cake is collected on a filter, suspended into 10 liters of 0.8 M NaCl and filtered. The limpid filtrate is washed by stirring with 2 liters of chloroform. After separation of the chloroform phase, the water phase is filtered again and precipitated by means of 1.5 volumes of ethyl alcohol. The precipitate is then washed and dehydrated with alcohol, and then dissolved into 100 mls of water. The solution is filtered by means of a membrane and lyophilized.

Yield: 6.9 of white-ivory powder having the following characteristics:
Solubility in water: Complete
Rotation $[\alpha]_D^{20} = -24°$
Huronic acids: 31.2%
Hexosamine: 33.1%
(organic) $SO_4^{--}$: 22.8%
Anticlotting activity: 28 U/mg (USP)
Clearing activity: 115-ILU/mg
Antithrombotic/Anticlotting activity: 2.

The heteropolysaccharide of the present invention, as obtained by the process above has been tested to assess the pharmacological properties and activities thereof.

Acute Toxicology

When administered to guinea pigs, rats, mice and rabbits, no toxic symptoms resulted up to a dose of 400 mg/Kg.

| | | | | |
|---|---|---|---|---|
| LD$_{50}$ | i.p. | (mouse) | 1615 | mg/Kg |
| | oral | (mouse) | >6000 | mg/Kg |
| | i.v. | (mouse) | 1000 | mg/Kg |
| LD$_{50}$ | i.p. | (rat) | 1463 | mg/Kg |
| | oral | (rat) | >6000 | mg/Kg |
| | i.v. | (rat) | 150 | mg/Kg |

Clearing activity test (1) Ediol Test: 100–50 ILU/mg
(2) Triton Test: serum lipid in triton-treated rats are significantly reduced by administered HP-80.
(3) Atherogenic diet test: when added at the dose of 1% to a semipurified diet supplemented with cholesterol and cholic acid, HP-80 is able to lower the serum lipids in rabbits.

In vitro anti-clotting and anti-thrombotic activities

Anticlotting activity (USP): 25–40 U/mg
Kaolin-Cephalin clotting time (KCCT): 14–22 U/mg
Yin's test/KCCT: 1.8–2.5 (Heparin=1)

Antithrombotic activity

A statistically significant effect on the movement of the thrombus is obtained, as determined by Chandler loop on rat plasma. In the light of the above activities a therapeutic use is foreseen, by oral and parenteral routes at daily dosages of 100 to 200 mg for the following cases:

Prevention of post-operative thrombo-embolisms.
Prevention of thrombotic occurrences following a thrombohenic status, such as for example that occuring in fertile women subjected to a prolonged treatment with oral contraceptives.
Prevention of deep vein thrombosis.
Prevention of hypercoagulability states.
Correction of the hyperdislipidemic states (hyperdislipoproteinamia).

By percutaneous route, the following therapeutic uses are indicated:

Thrombophlebitis, phlebitis, contusions, and hematomas.

What we claim is:

1. A process for obtaining hexuronyl hemoxaminoglycane sulfate, consisting essentially of
   Hexosamines: 29±3%
   Huronic acids: 27±3%
   (organic) SO$_4$−−:27±4%
   Acetyl groups: 7±1%
   Sodium: 10±2%
   such that the molar ration of buronic acids: hexosamine: sulfate:acetyl:sodium is 1:1.2:2:1.2:3
   PM (chromatography by exclusion on gel): 8.000–16.000
   Specific rotary power $[\alpha]_D^{20} = -30°/-15°$
   Electrolhoresis on cellulose acetate (buffer: pyridine-acetic-acid-water=1:10:229, pH 4.5 and development with toluidine blue): one main band with electrophoretic mobility $U=1.90-1.95\times10^{-4}$ cm$^2$v$^{-1}$s$^{-1}$
   I.R. spectrum: characteristic bands are observed at 1740, 1647, 1555, 1375, 1235 and 1050 cm$^{-1}$
   solubility: soluble in water, in diluted mineral acids and diluted fixed alkalies but insoluble in ethanol, comprising the steps of
   (a) hydrolyzing an animal organ, which has been ground and suspended in water, with a proteolytic enzyme,
   precipitating the limpid liquid by a water miscible solvent,
   (c) solubilizing the precipitate in a solution of a salt of a strong mineral acid with an alkali metal, alkaline-earth metal or ammonium, said saline solution having a ionic power corresponding to that of 0.8 M NaCl,
   (d) adding at a temperature not higher than 80° C. an excess of quaternary ammonium halide, selected from those having in their molecule at least one aliphatic group containing more than 12 carbon atoms, whereby a complex is formed which remains in solution, and separating the simultaneously formed precipitate,
   (e) precipitating the complex by dilution with water until an ionic power not higher than that of 0.4 M NaCl is obtained,
   (f) isolating the precipitated complex and solubilizing said complex in a salt solution having the same characteristics of that of step (c), and
   (g) precipitating of the hexuronyl hexosaminoglycane sulfate with a water miscible solvent and drying thereof.

2. A process according to claim 1 wherein the tissue employed is lung tissue.

3. A process as claimed in claim 1, characterized in that the hydrolysis with proteolytic enzyme is carried out on lung or duodenum tissue.

4. A process as claimed in either one of claim 1 or claim 3, characterized in that the proteolytic enzyme is selected from papain, bromelin, ficin, and bacterial proteolytic enzyme.

5. A process as claimed in claim 1, characterized in that the enzymatic hydrolysis is carried out under heat and until the value of the α-aminic nitrogen no longer varies.

6. A process as claimed in claim 1, characterized in that the hydrolysis with the proteolytic enzyme is continued for at least 3 hours.

7. A process as claimed in claim 1, characterized in that the said water-miscible solvent of the hydrolysis limpid liquid is selected from acetone, dioxane, methanol and ethanol.

8. A process as claimed in claim 1, characterized in that the said quaternary ammonium halide is selected from chlorides and bromides of cetylpyridinium and cetyltrimethylammonium.

9. A process as claimed in claim 1, characterized in that the excess of quaternary ammonium halide is at least 0.5 g per Kg of the starting organ.

10. A process as claimed in claim 1, characterized in that the said water-miscible solvent in the final precipitation step (step g) is acetone.

* * * * *